US006290974B1

(12) United States Patent
Swaisgood et al.

(10) Patent No.: US 6,290,974 B1
(45) Date of Patent: Sep. 18, 2001

(54) PROTEIN INGREDIENT FOR CARRYING LIPOPHILIC NUTRIENTS

(75) Inventors: Harold E. Swaisgood, Raleigh; Qiwu Wang, Garner; Jonathan C. Allen, Cary, all of NC (US)

(73) Assignee: North Carolina State University, Raleigh, NC (US)

( * ) Notice: Subject to any disclaimer, the term of this patent is extended or adjusted under 35 U.S.C. 154(b) by 0 days.

(21) Appl. No.: 09/009,104

(22) Filed: Jan. 20, 1998

(51) Int. Cl.$^7$ ................................ A61K 6/00; A61K 7/00; A61K 47/00; A61K 9/68; A23K 1/17
(52) U.S. Cl. ...................... 424/401; 424/439; 424/440; 424/442
(58) Field of Search ..................................... 424/401, 439, 424/440, 442

(56) References Cited

PUBLICATIONS

Allen and Swaisgood, Applications for Purified Whey Protein Fractions Derived from Bioselective Adsorption Affinity Chromotography: Continuation, *SDFRC 1997 Semi–Annual Reporty,* pp. 36, 38–39 (1997).
Allen et al.; Binding of Retinoids to β–Lactoglobulin Isolated With Bioselective Adsorption, *The Faseb Journal,* 10(3):A751–A752, Abstract 4350, Mar. 1996.
Allen et al.; Applications for Purified Whey Protein Fractions Derived from Bioselective Adsorption Affinity Chromatography, Southeast Dairy Foods Research Center, SDFRC Annual Report 95–96:19–21 (Jul. 1996).
Wang et al; β–Lactoglobulin Binds Vitamin D and Cholesterol, American Chemical Society, Annual Meeting Aug. 1996, Abstract 057.
Chen et al.; Purification and Characterization of β–Structural Domains of β–Lactoglobulin Liberated by Limited Proteolysis, *Journal of Protein Chemistry,* 12(5):613–625 (1993).
Jang et al.; Analysis of Ligand Binding and β–Lactoglobulin Denaturation by Chromatography on Immobilized Trans-Retinal, *J. Dairy Sci.,* 73(8):2067–2074 (1990).
Wang et al.; Characteristics of β–Lactoglobulin Binding to the All–Trans–Retinal Moiety Covalently Immobilized on Celite, *J. Dairy Sci.,* 76(7):1895–1901 (1993).
Wang et al.; Binding of Retinoids to β–Lactoglobulin Isolated by Bioselective Adsorption, *J. Dairy Sci.,* 80(6):1047–1053 (1997).
Wang et al., Binding of Vitamin D and Cholesterol to β–Lactoglobulin, *J. Dairy Sci.,* 80(6):1054–1059 (1997).
Dufour et al.; Binding of retinoids and β–carotene to β–lactoglobulin. Influence of protein modifications, *Biochimica et Biophsica Acta,* 1079:316–320 (1991).

Dufour et al.; β–Lactoglobulin binds retinol and protoporphyrin IX at two different binding sites, *Febs Letters,* 277(1,2):223–226 (Dec. 1990).
Flower et al.; Structure and sequence relationships in the lipocalins and related proteins, *Protein Science,* 2:753–761 (1993).
Frapin et al.; Probing the Fatty Acid Binding Site of β–Lactoglobulins, *J. of Protein Chemistry,* 12(4):443–449 (1993).
Jasminka Godovac–Zimmermann; The structural motif of β–lactoglobulin and retinol–binding protein: a basic framework for binding and transport of small hydrophobic molecules?, *TIBS* 13:64–66 (Feb. 1988).
Clement Ip et al., Retention of conjugated linoleic acid in the mammary gland is associated with tumor inhibition during the post–initiation phase of carcinogenesis, *Carcinogenesis,* 18(4):755–759 (1997).
Clement Ip et al.; Mammary Cancer Prevention by Conjugated Dienoic Derivative of Linoleic Acid, *Cancer Research,* 51:6118–6124 (1991).
Monaco et al.; Crystal Structure of the Trigonal Form of Bovine Beta–lactoglobulin and its Complex with Retinol at 2.5 ÅResolution, *J. Mol. Biol.,* 197:695–706 (1987).
M.Z. Papiz et al.; The structure of β–lactoglobulin and its similarity to plasma retinol–binding protein, *Nature vol.,* 324:383–385 (Nov. 1986).
Pérez et al.; Interaction of β–Lactoglobulin with Retinol and Fatty Acids and Its Role as a Possible Biological Function for This Protein: A Review, *J. Dairy Sci.,* 78(5):978–988 (1995).
Puyol et al.; Interaction of Bovine β–Lactoglobulin and Other Bovine and Human Whey Proteins with Retinol and Fatty Acids, *Agric. Biol. Chem.,* 55(10):2515–2520 (1991).
Spector et al.; Binding of Long Chain Fatty Acids to β–Lactoglobulin, *Lipids,* 5(4):401–411.
Palet et al.; Vitamin $B_{12}$ Derivatives as Anion Carriers in Transport through Supported Liquid Membranes and Correlation with Their Behavior in Ion–Selective Electrodes, *Anal. Chem.* 65:1533–1536 (1993).
Palet et al, Vitamin B12 Deriv as Anion Carriers in Transport AN 118:224423—CA See Abstract, 1993.*

* cited by examiner

Primary Examiner—Theodore J. Criares
Assistant Examiner—Jennifer Kim
(74) *Attorney, Agent, or Firm*—Myers Bigel Sibley & Sajovec (57) ABSTRACT

The present invention provides compositions comprising complexes of β-lactoglobulin with particular lipophilic nutrients, in particular vitamin E and vitamin $K_1$. Preferably, bioselective absorption is employed to isolate β-Lg for use as a carrier protein. Also provided are food compositions and topical compositions comprising complexes of β-lactoglobulin and a lipophilic nutrient.

30 Claims, 8 Drawing Sheets

PROTEIN INGREDIENT FOR CARRYING LIPOPHILIC NUTRIENTS

FIELD OF THE INVENTION

The present invention relates to complexes of proteins and lipophilic nutrients and method of making the same. In particular, the present invention concerns the use of complexes formed between protein carriers and particular lipophilic nutrients as a food additive.

BACKGROUND OF THE INVENTION

Beta-lactoglobulin (β-Lg) is the most abundant whey protein in bovine milk. β-Lg represents up to 50% of whey proteins in the milks of ruminants and some nonruminants such as horses, pigs, dogs, dolphins, kangaroos, cats, and whales, but is absent from the milks from humans, rodents and lagomorphs. Perez and Calvo, (1995) *J. Dairy Sci.* 78, 978. β-Lg is a 162 amino acid polypeptide with five cysteine residues, four of which participate in intramolecular disulfide bonds. There are two major β-Lg variants, designated β-Lg A and β-Lg B, which differ at two amino acid positions. Swaisgood, (1982) *Developments in Dairy Chemistry* 1, 1–59 (Fox, P. F., ed.), Applied Science Publishers, London.

In the ruminant, β-Lg primarily exists as a dimer, but is present as an 18,000 Da monomer in the milk of pigs, horses and donkeys. Perez and Calvo, (1995) *J. Dairy Sci.* 78, 978. Self-association to form dimers is affected by pH. Chen et al., (1993) *J. Protein Chem.* 12, 613. Alterations in the pH have also been reported to promote tetramerization of β-Lg to form an octomer. Kumosinski and Timasheff, (1966) *J. Am. Chem. Soc.* 88, 5635.

Analysis of the crystal structure of β-Lg indicates that the core of the molecule contains eight strands of β-sheets, which form an anti-parallel β-barrel (i.e., a calyx), with an α-helix and another β-strand on the surface of the protein. Monaco et al., (1987) *J. Mol. Biol.* 197, 695. The interior of the calyx is hydrophobic. The three-dimensional structure of β-Lg is very similar to that of retinol-binding protein (RBP), the primary transporter of retinol in serum, although there is only a 25–30% homology in amino acid sequence between these two proteins. Godovac-Zimmermann, (1988) *TBS* 13, 64.

SUMMARY OF THE INVENTION

The low solubility of lipophilic nutrients (such as fat-soluble vitamins) poses a problem for the food industry. It is often difficult to maintain lipophilic nutrients in low-fat foods because they come out of solution and/or absorb to packaging materials. There is a need in the art for methods of providing lipophilic nutrients as food additives.

Accordingly, it is an object of the present invention to provide complexes of β-Lg and lipophilic nutrients for use as food additives, particularly in low-fat foods. Another object of the invention is to provide infant formulas, dietary supplements (e.g. nutrient and vitamin supplements), and topical compositions containing the disclosed β-Lg/nutrient complexes. β-Lactoglobulin is highly soluble in aqueous solutions and acts as an effective carrier protein for lipophilic nutrients. Furthermore, bioselective absorption is employed to isolate β-Lg for use as a carrier protein. β-Lg prepared by bioselective absorption exhibits superior properties as a lipophilic carrier protein.

As a first aspect, the present invention provides a composition comprising a complex comprising β-lactoglobulin and a lipophilic nutrient selected from the group consisting of vitamin E and vitamin $K_1$.

As a second aspect, the present invention provides a food composition comprising a complex comprising β-lactoglobulin and a lipophilic nutrient. In preferred embodiments, the lipophilic nutrient is vitamin A, vitamin D, vitamin E, vitamin $K_1$, cholesterol, or conjugated linoleic acid.

As a third aspect, the present invention provides a dietary supplement comprising a complex comprising β-lactoglobulin and a lipophilic nutrient. In preferred embodiments, the lipophilic nutrient is vitamin A, vitamin D, vitamin E, vitamin $K_1$, cholesterol, or conjugated linoleic acid.

As a fourth aspect, the present invention provides a method of manufacturing a food composition comprising a complex comprising β-lactoglobulin and a lipophilic nutrient, comprising the steps of: (a) purifying β-lactoglobulin by affinity purification; (b) forming a complex between the purified β-lactoglobulin of step a and a lipophilic nutrient; and (c) manufacturing a food composition comprising the complex formed between the isolated β-lactoglobulin and the lipophilic nutrient of step b.

As a fifth aspect, the present invention provides a topical composition comprising a complex comprising β-lactoglobulin and a lipophilic nutrient in a topical carrier. Preferably, the lipophilic nutrient is vitamin A or vitamin E.

These and other aspects of the present invention are disclosed in more detail in the description of the invention below.

BRIEF DESCRIPTION OF THE DRAWINGS

FIG. 5 is a graphical representation of the fluorescence data plotted according to Equation [1], provided in Example 3. $P_T$=total protein concentration; $R_T$=total ligand concentration; and α=fraction of unoccupied ligand sites on the protein.

DETAILED DESCRIPTION OF THE INVENTION

The present invention is based on the discovery that β-Lg forms complexes with vitamin D, vitamin E, vitamin K, cholesterol, and conjugated linoleic acid. Further disclosed is the use of β-Lg as a carrier for lipophilic nutrients in foods, particularly low-fat foods, and more particularly dairy foods and low-fat dairy foods. β-Lg is a highly soluble protein, and binding of lipophilic nutrients to β-Lg will maintain these nutrients in solution in low-fat foods. Also disclosed is the use of β-Lg as a carrier for lipophilic nutrients in dietary supplements (e.g. vitamin supplements or nutrient supplements), infant formulas, and topical compositions.

Vitamin A, vitamin D, vitamin E, and vitamin K can be from any source known in the art for use in the present invention. The term "vitamin A" as used herein refers to any form of vitamin A, including but not limited to, retinol, retinaldehydes, retinal, retinoic acid (also known as tretinoin and retin-A), and vitamin A salts and derivatives (e.g., retinol palmitate, retinyl acetate, and β-carotene and other carotenoids). Preferably, the complex is formed between β-Lg and retinol, retinal or retinoic acid, or salts and derivatives thereof. The term "vitamin D" as used herein refers to any form of vitamin D, including but not limited to, ergocalciferol ($D_2$), cholecalciferol ($D_3$), 22,23-dihydroergocalciferol (D4), and vitamin D salts and derivatives (e.g., 25-hydroxycholecalciferol and 1-α,25-dihydroxycholecalciferol). Preferably, complexes are formed between β-Lg and ergocalciferol ($D_2$) or cholecalciferol ($D_3$), or salts and derivatives thereof. The term "vitamin E" as used herein refers to the family of compounds known as tocopherols (e.g., α-tocopherol, β-tocopherol, δ-tocopherol, γ-tocopherol), as well as tocol, tocoquinone, tocotrienol, and vitamin E salts (e.g., vitamin E phosphate) and derivatives (e.g., tocopherol sorbate, tocopherol acetate, tocopherol succinate, other tocopherol esters). Preferably, complexes are formed between β-Lg and α-tocopherol, or salts and derivatives thereof. As used herein, the term "vitamin K" refers to vitamin $K_1$ (phytonadione), vitamin $K_2$ (menaquinone), vitamin $K_3$ (menadione), vitamin $K_4$, vitamin $K_5$, vitamin K6, vitamin $K_7$, and their salts and derivatives. Vitamin $K_1$, and vitamin $K_2$ and salts and derivatives thereof, are preferred for use in the present invention, with vitamin $K_1$, and salts and derivatives thereof, being more preferred.

As used herein, conjugated linoleic acid is a collective term referring to a mixture of positional and geometric dienoic derivatives of linoleic acid, and salts and derivatives thereof (e.g. methyl esters). See Ip et al., (1991) Cancer Res. 51, 6118. The two double bonds in conjugated linoleic acid are primarily in positions 9 and 11, or in positions 10 and 12. The double bonds can be either cis or trans. Id. Conjugated linoleic acid for use in the present invention may be from any source, for example, it can be produced by chemical synthesis, with or without the use of rumen microorganisms, or it can be isolated from natural sources.

Conjugated linoleic acid isomers and conjugated linoleic acid methyl esters are the subject of increasing interest because of their reported anti-cancer activities. See, e.g., Ip et al., (1997) Carcinogenesis 18, 755; Ip et al., (1991) Cancer Res. 51, 6118. Conjugated linoleic acids are found in many foods, in particular animal products. Rumen microorganisms synthesize conjugated linoleic acid from linoleic acid, and ruminant tissues and milk contain relatively high levels of conjugated linoleic acid. Dairy products are considered an important dietary source of conjugated linoleic acid. Lin et al., 91995) J. Dairy Sci. 78, 2358. Conjugated linoleic acids and their methyl esters are removed or reduced in non-fat or low-fat foods, and it is desirable to add these nutrients back to non-fat and low-fat foods because of their anti-cancer effects.

According to the present invention, cholesterol can be from any source, and the term "cholesterol" also encompasses cholesterol salts and derivatives (e.g. 7-dehydroxycholesterol). Cholesterol is typically considered undesirable in adult diets, but it is an important nutrient for infants. The present invention provides food compositions (e.g., infant formulas), dietary supplements, and topical compositions containing the disclosed β-Lg/cholesterol complexes.

It is known that β-Lg from ruminant milk binds retinol and fatty acids. Perez and Calvo, (1995) J. Dairy Sci. 78, 978; Cho et al., (1994) J. Biol. Chem. 269 11102; Frapin et al., (1993) J. Protein Chem. 12 443. The biological function of β-Lg is unknown, but it has been suggested that β-Lg binds retinol and assists in its uptake by the intestine in the neonate. Perez and Calvo, (1995) J. Dairy Sci. 78, 978; Godovac-Zimmermann, (1988) TIBS 13, 64. β-Lg has also been reported to bind other small hydrophobic molecules in vitro, such as alkanone flavors (O'Neill and Kinsella, (1987) J. Agric. Food Chem. 35, 770), polyoxyethylene sorbitan monolaurate (Coke et al., (1990) J. Colloid Interface Sci. 138, 489), protoporphyrin IX (Dufour et al., (1990) FEBS Lett. 277, 223), aromatic compounds (Farrell et al., (1987) J. Dairy Sci. 70, 252), and ellipticine (Dodin et al., (1990) Eur. J. Biochem. 193, 697).

Retinol appears to bind in the hydrophobic calyx of β-Lg, although a second retinol binding site on the surface of the molecule has been proposed. Monaco et al., (1987) J. Mol. Biol. 197, 695. The fatty acid binding site may be located in the hydrophobic calyx as well. The binding of β-Lg to fatty acids in ruminant milk has been estimated at 1.0 to 1.4 mol·$mol^{-1}$ protein dimer, and it has been suggested that in vivo β-Lg functions primarily as a fatty acid binding protein rather than a retinol carrier. Perez and Calvo, (1995) J. Dairy Sci. 78, 978.

β-Lactoglobulin for use in the present invention can be from a recombinant or natural source. Naturally-occurring sources of β-Lg include skim milk, whole milk, and whey. The term "β-Lg" includes β-Lg variants, including but not limited to β-Lg A and β-Lg B. It is known that β-Lg can exist as a monomer or form higher-order structures such as dimers and octomers. Complexes between β-Lg and lipophilic nutrients according to the present invention can contain β-Lg monomers, dimers, octomers, or a mixture of these forms. β-Lactoglobulin can be from any mammalian species of origin, preferably from a ruminant species, more preferably of bovine origin. Furthermore, the term β-Lg includes fragments of the β-Lg molecule that retain the ability to bind lipophilic nutrients. For example, it has been demonstrated that major fragments of the β-barrel domain can be produced by limited tryptic hydrolysis (Chen et al., 1993; Huang et al., 1994). Characterization of the 7.9 and 8.4 kDa fragments resulting from limited trypsin hydrolysis of β-Lg revealed that much of the original β-sheet structure was retained.

In preferred embodiments of the invention, the β-Lg is isolated or purified by a process including an affinity purification step. Exemplary methods include binding to an immobilized affinity ligand using affinity chromatography or a batch processing method (i.e., affinity precipitation with beads bearing affinity ligands), with affinity chromatography being preferred. Preferably, the affinity purification employs bioselection, wherein binding of β-Lg to the affinity ligand depends on the retention of the high affinity binding sites (in contrast to antibody binding to an epitope). Furthermore, the preferred ligand for bioselection is a retinoid derivative (i.e., the vitamin A family of molecules). Those skilled in the art will appreciate, however, that any affinity ligand showing sufficient specificity and avidity of binding to β-Lg can be employed to purify β-Lg according to the present invention.

Any suitable retinoid, including but not limited to, retinal, retinol, retinyl acetate, and retinoic acid can be immobilized to produce an affinity matrix, with retinal being preferred. Immobilization of retinal to a solid support has previously been described. Wang et al., (1997) J. Dairy Sci. 80, 1047; Wang et al., (1996) J. Agric. Food Chem. 44, 1664; Wang and Swaisgood, (1993) J. Dairy Sci. 76, 1895; and Jang and Swaisgood, (1990) J. Dairy Sci. 73, 2067.

All known methods for immobilization of ligands (by adsorption or by covalent bonds) and any solid support available to those skilled in the art may be employed in carrying out the present invention. Suitable support matrices include organic, biopolymer, and inorganic supports. Exemplary support matrices include porous beads formed from glass, silica, alumina, ground corn grits, cellulose, or CELITE™ (a commercially available form of diatomaceous earth; Celite Corp., Lompoc, Calif.). Typically, the support matrix is modified to bear reactive groups to facilitate the immobilization reaction. For example, primary amine groups can be attached to the support by using silanes for siliceous or alumina-based supports. The attached primary amine groups are activated by glutaraldehyde or other activating agent prior to the addition of the ligand. Crosslinking of the covalently bound affinity ligand is optional.

Illustrative examples of substrates useful for binding retinoids include controlled-pore glass beads (Jang and Swaisgood, (1990) J. Dairy Sci. 73, 2067), cellulose, aminopropyl-CELITE™ or succinamidopropyl-CELITE™ (Wang and Swaisgood, (1993) J. Dairy Sci 76, 1895; Huang et al., (1997) J. Biotechnology 53, 21). Substrates comprising CELITE™ derivatives are preferred, with aminopropyl-CELITE™ or succinamidopropyl-CELITE™ being more preferred.

The most preferred bioselective matrix for carrying out the present invention is an N-retinyl-CELITE™ affinity matrix as previously described. Wang and Swaisgood, (1997) J. Dairy Sci. 80, 1047; Wang and Swaisgood, (1993) J. Dairy Sci 76, 1895.

β-Lactoglobulin isolated by bioselective affinity purification (as described above) exhibits improved characteristics as compared with β-Lg purified by conventional techniques, such as ion exchange chromatography. Bioselective affinity purification selects for β-Lg molecules that retain sufficient higher-order structure to bind ligand. Accordingly, affinity-purified β-Lg preparations contain less denatured molecules than will β-Lg purified by exchange methods.

Moreover, most β-Lg in milk has fatty acids bound in the high-affinity site. Diaz de Villigas et al. (1987) Milchwissenschaft 42, 357; Perez and Calvo, (1995) J. Diary Sci. 78, 978. While not wishing to be held to any theory of the invention, it appears that affinity purification of β-Lg, as described above, selects for β-Lg with unoccupied binding sites and/or displaces fatty acids from the binding site. Thus, according to embodiments of the invention in which β-Lg is isolated by bioselective affinity methods, the capacity of the isolated ,-Lg for compounds binding to fatty acids binding sites is enhanced over β-Lg isolated by other methods. In particular, binding of vitamin A, vitamin D, vitamin E, vitamin $K_1$, cholesterol, and conjugated linoleic acid to β-Lg is enhanced.

β-Lactoglobulin forms specific and high-affinity complexes with particular lipophilic nutrients, such as vitamin A, vitamin D, vitamin E, vitamin K, cholesterol, and conjugated linoleic acid. The dissociation constant of the claimed complexes between β-Lg and lipophilic nutrients are at least $10^{-7}$ M, preferably at least $10^{-8}$ M, more preferably at least $10^{-9}$ M. The complexes can be formed by simply mixing β-Lg and the lipophilic nutrient (typically in solution) together. Preferably, the β-Lg is substantially free of other proteins, and is at least 80%, 85%, 90%, or even 95% or more pure. More preferably, the β-Lg is purified by bioselective affinity purification as described above. Complexes can be formed between β-Lg and more than one lipophilic nutrient; the β-Lg/lipophilic nutrient complexes disclosed herein may be associated with additional molecules, for example, fatty acids or molecules bound by non-specific interactions.

Complexes of the present invention find use as food additives and dietary supplements (e.g., vitamin or nutrient supplements). In one embodiment, the β-Lg/nutrient complex can be dried down by any means known in the art, such as precipitation and lyophilization or lyophilization alone, to produce a dried product. The dried complex is convenient for use as a food additive, and in forming nutrient and vitamin supplements, with food additives and vitamin supplements being preferred. Vitamin K, for example, cannot easily be obtained in solid form, and vitamin K supplements are usually provided as a liquid gel. The present invention provides a means of forming vitamin K tablets, in particular chewable vitamin K tablets. Nutrient and vitamin supplements can be in any form known in the art, including but not limited to, tablets (including chewable tablets), capsules, gel-caps, powders, elixirs, and effervescent tablets. Alternatively, nutrient and vitamin supplements can be in the form of shakes, juices or other drinks, and bars.

The disclosed complexes also find use as a component of tissue culture media to promote growth, differentiation and/or viability of cultured cells. It has previously been shown that β-Lg can be employed as a fatty acid carrier in cell culture. Perez and Calvo, (1995) J. Diary Sci. 78, 978. The disclosed complexes further find use in methods of quantifying or purifying vitamin A, vitamin D, vitamin E, vitamin K, cholesterol, and conjugated linoleic acid. The disclosed complexes are also useful in any assay that relies upon the use of selective binding partners.

The present invention also provides food compositions containing complexes of β-Lg and lipophilic nutrients. Preferably the lipophilic nutrients are vitamin A, vitamin D, vitamin E, vitamin $K_1$, cholesterol, conjugated linoleic acid, essential fatty acids, and other fatty acids. More preferably, the food compositions contain complexes of β-Lg with vitamin A, vitamin D, vitamin E, vitamin $K_1$, and conjugated linoleic acid. Even more preferred are food compositions containing β-Lg complexes with vitamin E, vitamin $K_1$, and conjugated linoleic acid. Because of its availability, excellent nutritional qualities, and high solubility, β-Lg is highly desirable as a carrier for lipophilic nutrients in food compositions. In particular, β-Lg is useful as a carrier for lipophilic nutrients in low-fat foods, more preferably low-fat dairy foods. Complexes of P-lactoglobulin and lipophilic nutrients are also useful for fortifying infant formulas.

The presently-claimed food compositions are formed by combining a β-Lg complex according to the present invention with other food ingredients. Alternately stated, a food composition is a food product containing a β-Lg complex of the present invention. A food composition can be a liquid or a solid food for human or animal consumption, and includes, but is not limited to, dairy products, processed meats, breads, cakes and other bakery products, processed fruits and vegetables, etc. Dairy products are preferred. Exemplary dairy products include milk, butter, cheese, yogurt, ice cream and other frozen desserts, whipped toppings, cream, custard, pudding, and chocolate.

As defined herein "low-fat" indicates a food having equal to or less than 5%, 3%, 2%, 1%, 0.5%, 0.1% or even 0.01% (w/w) fat. "Low-fat" foods include "non-fat foods," i.e., those having essentially no fat therein (or only a negligible amount), such as skim milk. Alternatively, a low-fat food is one that has a reduced amount of fat as compared to what is normally found in the food. Thus, for example, a low-fat imitation ice cream may have greater than 5 % (w/w) fat, but it has less fat than is normally found in ice cream.

In a preferred embodiment of the invention, the disclosed complexes between β-Lg and a lipophilic nutrient as used as food additives to fortify dairy foods, more preferably low-fat dairy foods. Exemplary low-fat dairy foods include but are not limited to low-fat milks (e.g., milk having less fat than whole milk, and milks having 2%, 1%, 0.5% (w/w) fat or skim milk), low-fat cheeses and cheese products, low-fat yogurt, low-fat frozen desserts (e.g. ice milk, frozen yogurt), low-fat spreads, low-fat puddings and custards, and low-fat chocolates.

β-Lactoglobulin is a natural component of many milks, and is therefore an acceptable additive to dairy food products. Moreover, diary products are normally a good source of lipophilic nutrients, such as fat-soluble vitamins and conjugated linoleic acid, but these nutritional characteristics are compromised in low-fat products. As described above, the lipophilic nutrients have a tendency to come out of solution and to adhere to materials that are commonly used to package low-fat products, such as lipophilic or polymeric materials.

Accordingly, the present invention further provides food compositions, dairy food compositions, and low-fat dairy and non-dairy foods in containers or cartons with polymeric or lipophilic inner surfaces. In particular, the present invention encompasses milk, low-fat milks (e.g., low-fat milks having 2%, 1%, 0.5% (w/w) fat or skim milk) in containers or containers, the interior surface of which is a lipophilic (e.g., waxy) or polymeric (e.g., polyethylene or high density polyethylene) material.

Also disclosed herein are topical compositions for use in personal care and/or hygiene containing the β-Lg/nutrient complexes disclosed herein (e.g., soaps, skin creams, soaps, cleansers, shampoos). Topical compositions containing complexes of β-Lg with vitamin E, vitamin A, conjugated linoleic acid, and essential fatty acids are preferred, with complexes between β-Lg and vitamin A or vitamin E being more preferred. The topical compositions disclosed herein are suitable for topical application to mammalian skin. The compositions comprise a safe and effective amount of the β-Lg complexes and other active agents, and a cosmetically- and/or pharmaceutically-acceptable topical carrier.

The phrase "cosmetically- and/or pharmaceutically-acceptable carrier", as used herein, means any substantially non-toxic carrier suitable for topical administration to the skin, which has good aesthetic properties, and is compatible with the β-Lg complexes of the present invention. By "compatible" it is meant that the β-Lg complexes will remain stable and retain substantial activity therein. The carrier can be in a wide variety of forms, such as sprays, emulsions, mousses, liquids, creams, oils, lotions, ointments, gels and solids.

Suitable pharmaceutically-acceptable topical carriers include, but are not limited to, water, glycerol, alcohol, propylene glycol, fatty alcohols, triglycerides, fatty acid esters, and mineral oils. Suitable topical cosmetically-acceptable carriers include, but are not limited to, water, petroleum jelly, petrolatum, mineral oil, vegetable oil, animal oil, organic and inorganic waxes, such as microcrystalline, paraffin and ozocerite wax, natural polymers, such as xanthanes, gelatin, cellulose, collagen, starch or gum arabic, synthetic polymers, alcohols, polyols, and the like. Preferably, because of its non-toxic topical properties, the pharmaceutically- and/or cosmetically-acceptable carrier is substantially miscible in water. Such water miscible carrier compositions can also include sustained or delayed release carriers, such as liposomes, microsponges, microspheres or microcapsules, aqueous based ointments, water-in-oil or oil-in-water emulsions, gels and the like.

The following Examples are provided to illustrate the present invention, and should not be construed as limiting thereof. The abbreviations used in the Examples are defined as follows: "g" means gram, "mg" means milligram, "$\mu$g" means microgram, "L" means liter, "mL" means milliliter, "mol" means mole, "M" means molar, "mM" means millimolar, $\mu$M means micromolar, "m" means meter, "mm" means millimeter, "nm" means nanometer, "Da" means daltons, "kDa" means kilodaltons, "w/v" means weight per volume, and "v/v" means volume per volume.

EXAMPLE 1

Materials

Vitamin $D_2$ (ergocalciferol, reference standard), vitamin $D_3$ (cholecalciferol, reference standard), vitamin $D_3$ sulfate (sodium salt, crystalline), vitamin E ($\alpha$-tocopherol), vitamin $K_1$ (2-methyl-3-phytyl-1,4-naptho-quinone), vitamin $K_3$ (menadione), cholesterol (grade 99+%), ergosterol (minimum 90%), 7-dehydrocholesterol (crystalline), linoleic acid, conjugated linoleic acid and its methyl ester, and N-acetyl-trypto-phanamide were purchased from Sigma Chemical Company (St Louis, Mo.). To prevent the oxidation and isomerization of these compounds, each was dissolved in absolute ethanol, ethyl ether, or buffer in the dark under anaerobic conditions. Solutions of the appropriate concentration (w/v) were prepared fresh daily and used without further assay.

EXAMPLE 2

Isolation of β-Lg from Whey

N-Retinyl-CELITE™ (R648, 501100 mesh) was prepared as previously described (Wang et al., (1993) *J. Dairy Sci.* 76, 1895) by reduction of the Schiff base formed with all-trans-retinal and aminopropyl-CELITE™ using $NaCNBH_3$. Acid whey was prepared from fresh pasteurized skim milk that had been obtained from the University Dairy Plant by isoelectric precipitation of the casein at pH 4.6. After removal of the casein precipitate, the whey was adjusted to pH 5.14 with 0.1 M NaOH and centrifuged (8600×g for 90 min) or passed through a 0.45-μm filter.

A column was packed with 500 ml of the bioadsorbant N-retinyl-CELITE™ and equilibrated with 0.05 M phosphate buffer, pH 5.14. While the elution at 280 nm was being monitored, 2 L of the whey at pH 5.14 was loaded on the column and then washed with the phosphate buffer at pH 5.14. When the values for the absorbance at 280 nm returned to the baseline, the eluting buffer was changed to 0.4 M phosphate at pH 7.0 to desorb the β-Lg. This protein preparation was diafiltered against distilled water, concentrated (Amicon YM 100 membrane; Amicon, Inc., Beverly, Mass.), and lyophilized.

The protein fractions were analyzed by size-exclusion chromatography using a SUPEROSE™ 12 HR 10/30 column (Pharmacia Biotech Inc., Piscataway, N.J.) incorporated in a Waters 990 system (Waters Corp., Milford, Mass.) or with a SSI 222B pump and a Linear UV-106 monitor (Linear Instruments Corp., Reno, Nev.) operating at 280 or 214 nm. Elution was with 20 mM Trizma·HCl containing 0.1 M NaCl and 0.02% sodium azide, pH 7.0, at a flow rate of 0.5 ml/min. Solutions of BSA, β-Lg, α-lactalbumin, and orotic acid served as standards.

Preparation of β-Lg by bioselective adsorption consistently yields a product that has 96% or more purity as determined by size-exclusion chromatography.

EXAMPLE 3

Flurescence Spectroscopy

Fluorescence spectra were recorded at 23 ° C. with a System 3 Scanning Spectrofluorometer (Optical Technology Devices, Inc., Elmsford, N.Y.) using the ratio mode. Excitation and emission spectra were obtained with 1 μM solutions of β-Lg in 50 mM sodium phosphate, pH 7.0, both in the presence and absence of 2 μM concentrations of the various ligands. Titration of β-Lg with the various ligands was quantified by measuring the fluorescence quenching of the protein tryptophanyl residues (excitation at 287 nm, emission measured at 332 nm). The spectrofluorometer cuvette contained 2.5 ml of 1 μM β-Lg in the phosphate buffer to which 2.5-μl increments of the ligand solution in ethanol or ethyl ether were added with a micropipette. Dufour et al., (1990) *FEBS Lett.* 277, 223. A solution of N-acetyl-rypto-phanamide that had an absorbance at 287 nm, which was equal to that of the protein solution, was titrated in a similar manner to serve as a blank (control) sample. Cogan et al., (1976) *Eur. J. Biochem.* 65, 71.

The titration can also be followed by measuring the increase in vitamin D or cholesterol fluorescence that was due to energy transfer from the tryptophanyl residue. Thus, with excitation at 287 nm, emission was measured at 412 nm for vitamin D or 390 nm for cholesterol.

The titration data can be used to evaluate the equilibrium dissociation constant and the number of binding sites per monomer as has been previously described. Cogan et al., (1976) *Eur. J. Biochem.* 65, 71; Dufour and Haertle, (1991) *Biochim. Biophys. Acta* 1079, 316; Wang et al., (1997) *J. Dairy Sci.* 80, 1047. The linear regression equation $$P_T a = (1/n)[R_T a/(1-a)] - K_d/n \qquad [1]$$

is used to calculate n, the number of binding sites per molecule of protein and $K_d$, the apparent dissociation constant. In this equation, $P_T$ is total protein concentration, and $R_T$ is total ligand concentration.

EXAMPLE 4

Binding of Various Forms of Vitamin D

Figure 1:
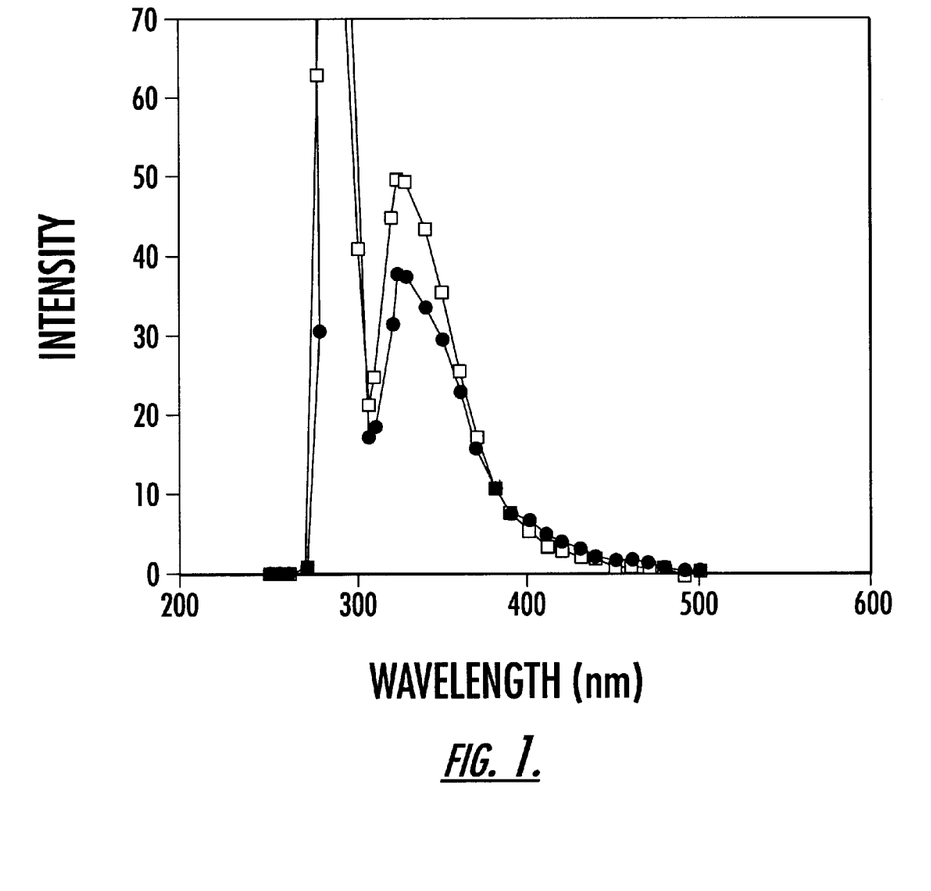
FIG. 1 is a graphical representation of the fluorescence emission spectra of β-Lg in the presence (•) or absence (□) of vitamin $D_2$. The excitation wavelength was 287 nm, and fluorescence emission was measured at 23° C. with a cell path length of 1 cm, a band width of 10 nm, and a scan speed of 50 nm/min. The protein concentration was 1 μM in 50 mM phosphate, pH 7.0, and the vitamin $D_2$ concentration was 2 μM.

Binding of hydrophobic ligands in proximity to $Trp_{19}$ results in energy transfer between this protein residue and the ligand, and thus changes in the fluorescence emission spectra can be used to follow complex formation. Fluorescence emission spectra of β-Lg with and without bound vitamin $D_2$ that result from excitation of tryptophanyl residues at 287 nm are shown in FIG. 1. The fluorescence of the protein was quenched between 300 and 360 nm, indicating that vitamin $D_2$ was bound. Preliminary studies indicated that vitamin $D_2$ exhibited an emission maximum at 412 nm; thus, if the vitamin was bound, energy transfer from the tryptophanyl residue should have increased the fluorescence at this wavelength.

Figure 2:
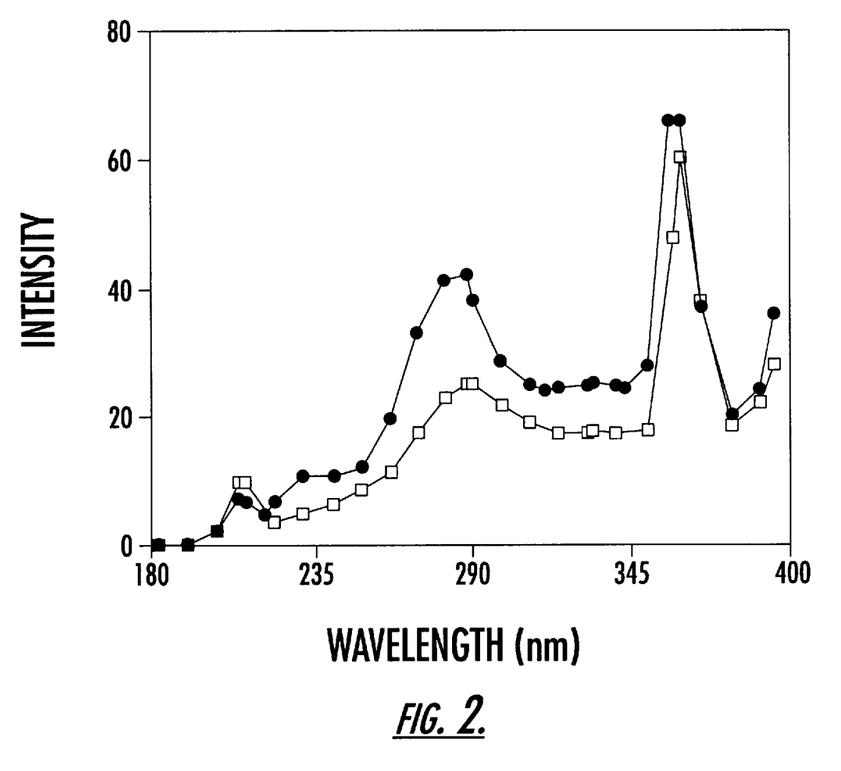
FIG. 2 is a graphical representation of the fluorescence excitation spectra of vitamin $D_2$ in the presence (•) or absence (□) of β-Lg. The excitation scan speed was 50 nm/min from 180 to 400 nm. Emission was measured at 412 nm. Spectra were obtained at 23° C. with 2 μM vitamin $D_2$ in 50 mM phosphate buffer, pH 7.0, and 1 μM β-Lg.

The excitation spectra of vitamin $D_2$ solutions in the presence and absence of β-Lg, with the emission measured at 412 nm, are shown in FIG. 2. Although vitamin $D_2$ also exhibited some absorption around 287 nm, in the presence of protein, fluorescence at 412 nm was increased by excitation around 287 nm, again indicating that the vitamin was bound in a site near $Trp_{19}$. The protein fluorescence emission at 332 mn is shown as a function of vitamin $D_2$ concentration in FIG. 3. The fluorescence quenching of the 1 μM protein solution appeared to reach a maximum at a vitamin $D_2$ concentration of 2 μM. Such titration experiments were performed five times, and the data were evaluated using Equation [1] from Example 3, yielding $K_d$=4.91±3.28 nM and n=2.00±0.16. Thus, the affinity of β-Lg for vitamin $D_2$ is about 10-fold greater than that for vitamin A and other retinoids. Cho et al., (1994) *J. Biol. Chem.* 269, 11102; Dufour and Haertle, (1991) *Biochim. Biophys. Acta* 1079, 316; Wang et al., (1997) *J. Dairy Sci.* 80, 1047. Typical values for the $K_d$ with retinol range from 36 (Wang et al., (1997) *J. Dairy Sci.* 80, 1047) to 44 nM (Dufour and Haertle, (1991) *Biochim. Biophys. Acta* 1079, 316). Furthermore, 2 mol·$mol^{-1}$ of protein appeared to be bound, but only 1 mol of the various retinoids was bound. Cho et al., (1994) *J. Biol. Chem.* 269, 11102; Dufour and Haertle, (1991) *Biochim. Biophys. Acta* 1079, 316; Wang et al., (1997) *J. Dairy Sci.* 80, 1047.

Figure 3:
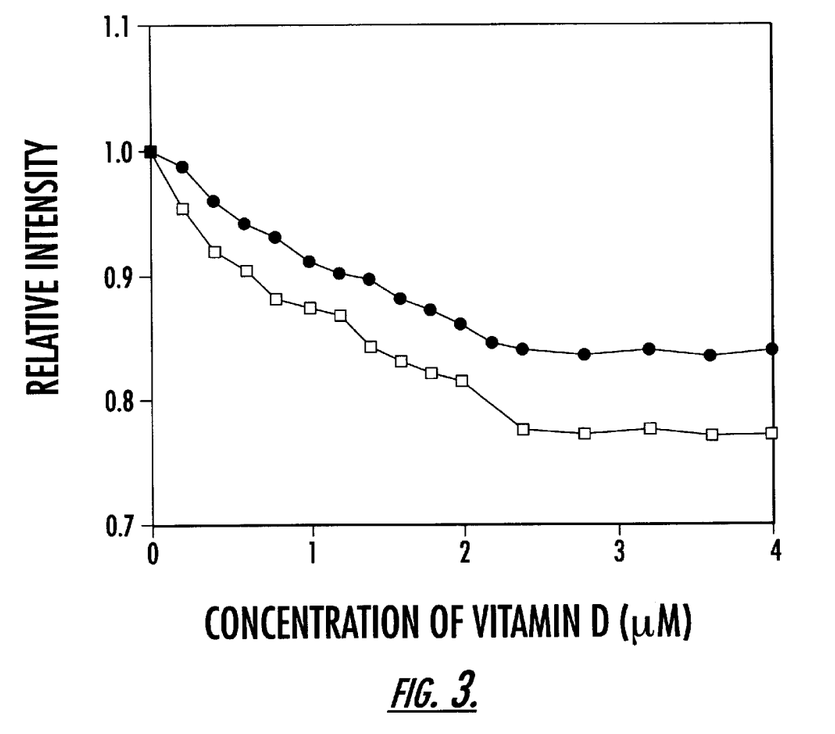
FIG. 3 is a graphical representation of the relative fluorescence intensities of β-Lg tryptophanyl residues measured at 332 nm with varying concentrations of vitamin $D_2$ (□) or vitamin $D_3$ (•). The fluorescence intensity of the 1 μM protein solution without ligand was used as the reference. The excitation wavelength was 287 nm.
Figure 4:
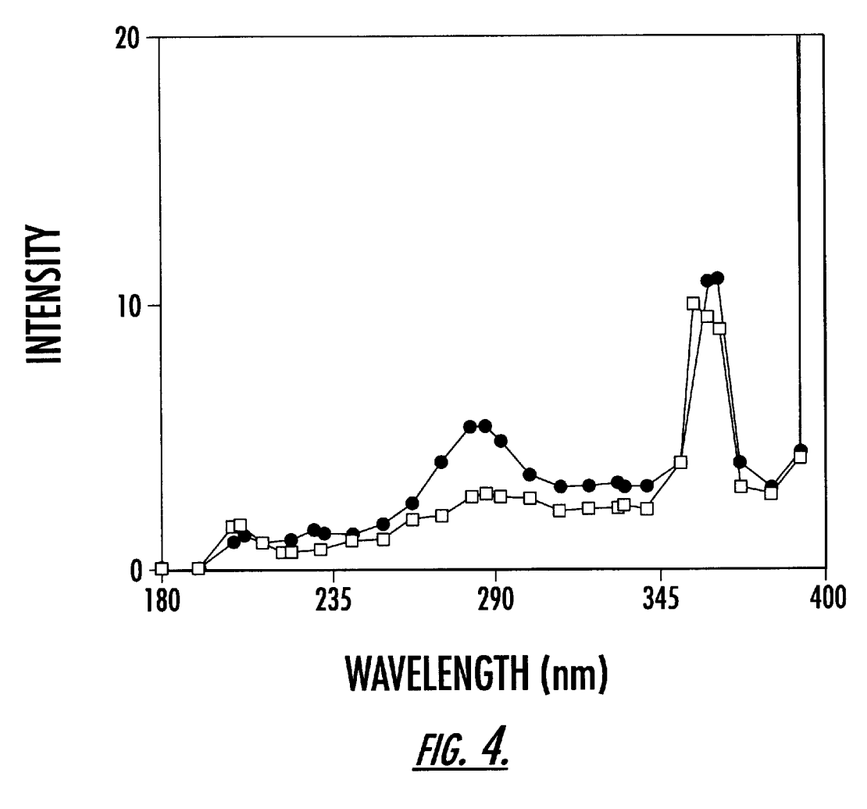
FIG. 4 is a graphical representation of the fluorescence excitation spectra of vitamin $D_3$ in the presence (□) or absence (•) of β-Lg. The excitation scan speed was 50 nm/min from 180 to 400 nm. Emission was measured at 412 nm. Spectra were obtained at 23° C. with 2 μM vitamin $D_3$ in 50 mM phosphate buffer, pH 7.0, and 1 μM β-Lg.
Figure 5A:
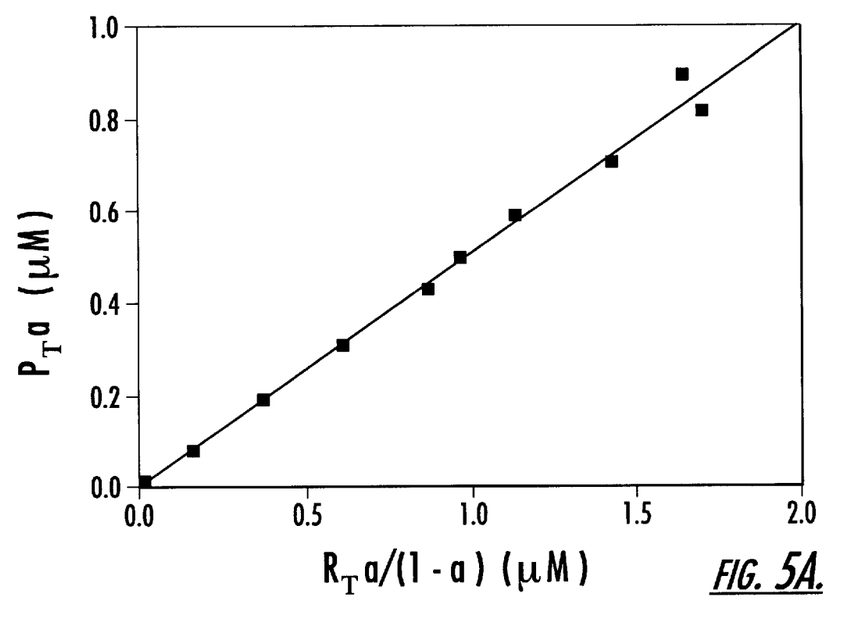
FIG. 5A shows the quenching of tryptophanyl fluorescence at 332 nm by varying concentrations of vitamin $D_3$ obtained from titration of 1 μM β-Lg solution.
Figure 5B:
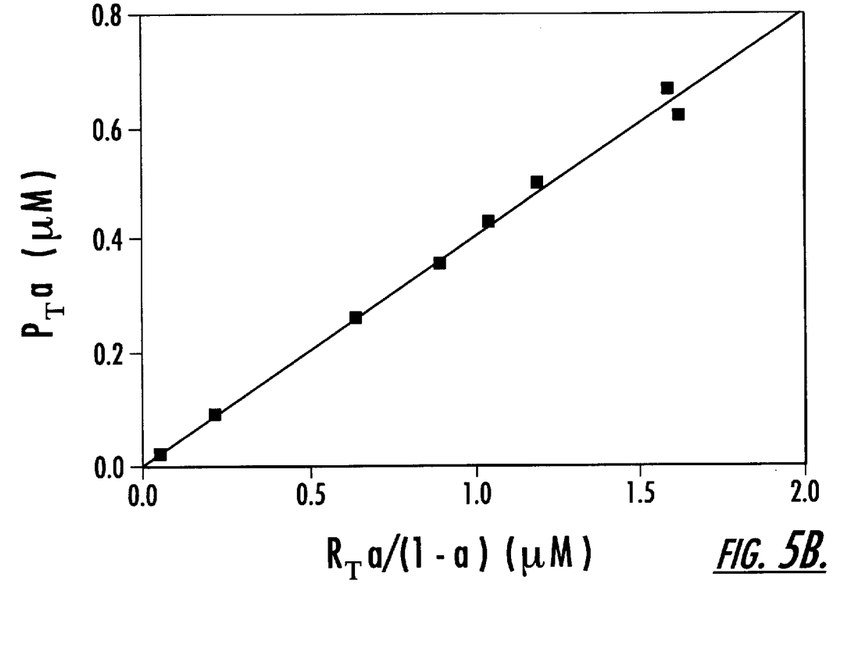
FIG. 5B shows the enhancement of vitamin $D_3$ fluorescence at 412 nm in the presence of varying concentrations of vitamin $D_3$.

Possible binding of vitamin $D_3$ to β-Lg was also investigated by recording the fluorescence emission at 412 nm as a function of the excitation wavelength for vitamin solutions with and without added β-Lg (FIG. 4). As with vitamin $D_2$, the increased intensity of fluorescence at 412 nm with excitation at 287 nm indicated binding of the vitamin and transfer of energy from protein tryptophanyl residues to the vitamin molecule. In a titration experiment, the protein fluorescence at 332 nm with excitation at 287 nm was determined as a function of vitamin $D_3$ concentration (FIG. 3). These data are plotted according to Equation [1] in FIG. 5A. In this manner, triplicate analyses provided the values for $K_d$ and n that are listed in Table 1. Also, the increase of vitamin $D_3$ fluorescence at 412 nm with excitation at 287 nm for varying vitamin concentrations can be plotted according to Equation [1] as shown in FIG. 5B. Triplicate analyses gave values for the $K_d$ and n that are listed in Table 1. Thus, the affinity for vitamin $D_3$ appeared to be similar to that for the retinoids; however, 2 molecules were bound per molecule of protein.

Similar analyses of the fluorescence changes that occurred when β-Lg was titrated with ergosterol and vitamin $D_3$ sulfate yielded the values for n and $K_d$ that are listed in Table 1, in which all the values for the ligand examined in this study are compared. The stoichiometry of the binding appears to be 2 mol~$mol^{-1}$ for each of these compounds, which formed a one-to-one complex. Dufour and Haertle, (1991) Biochim. Biophys. Acta 1079, 316; Wang et al., (1997) J. Dairy Sci. 80, 1047. However, the binding affinity appeared to be significantly greater for vitamin $D_2$ and ergosterol.

TABLE 1

Equilibrium dissociation constants and the stoichiometry of the interaction between β-LG and various lipophilic nutrients.[1]

| Compound | n (mol/mol of protein) | | $K_d$ (nM) | |
|---|---|---|---|---|
| | X | SD | X | SD |
| Vitamin $D_2$ (ergocalciferol) | 2.00 | $0.16^2$ | 4.91 | $3.28^2$ |
| Ergosterol | $2.02^3$ | | $6.25^3$ | |
| Vitamin $D_3$ (cholecalciferol) | 2.01 | 0.25 | 36.0 | 30.1 |
| Vitamin $D_3$ sulfate | 1.74 | 0.18 | 30.3 | 28.3 |
| 7-Dehydrocholesterol | 1.65 | 0.06 | 26.7 | 4.7 |
| Cholesterol | 2.36 | 0.09 | 34.9 | 8.0 |

[1]Unless noted otherwise, these values represent triplicate titrations of a single preparation. n = Number of binding sites per molecule of protein; $K_d$ = apparent dissociation constant.
[2]Result of five titrations of a single preparation.
[3]Result of a single titration.

EXAMPLE 5

Binding of Cholesterol

Figure 6:
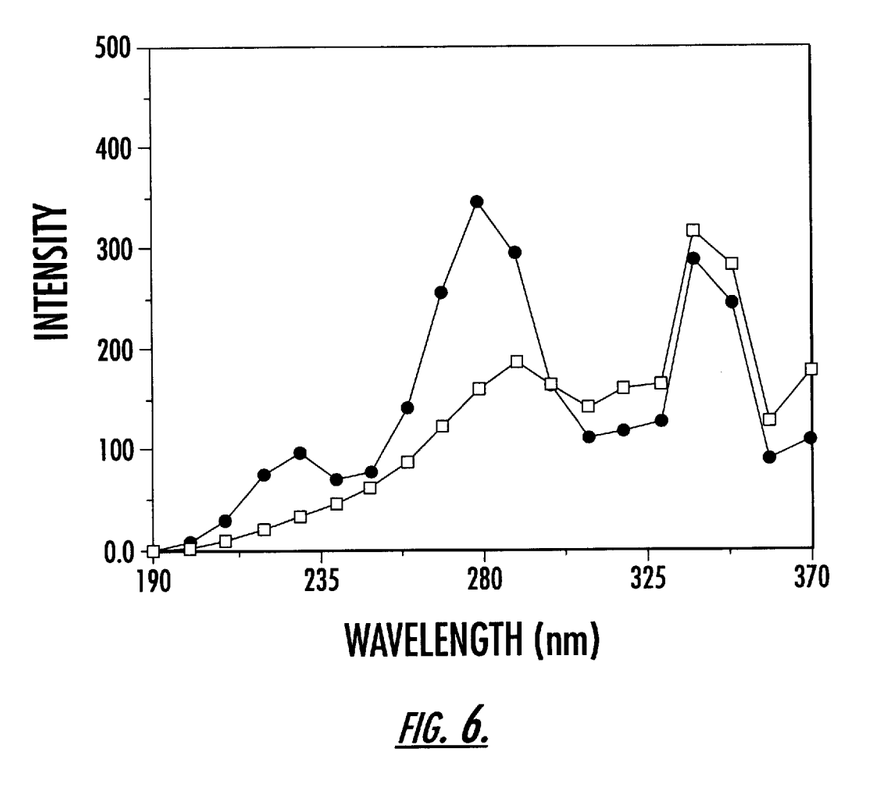
FIG. 6 is a graphical representation of the fluorescence excitation spectra of 7-dehydrocholesterol in the presence (□) and absence (•) of β-Lg. The excitation scan speed was 50 nm/min from 180 to 370 nm. Emission was measured at 390 nm. Spectra were obtained at 23° C. with 2 μM 7-dehydrocholesterol in 50 mM phosphate buffer, pH 7.0, and 1 μM β-Lg.

The potential binding of both cholesterol and 7-dehydrocholesterol to β-Lg was examined by fluorescence spectroscopy, essentially as described above for vitamin D (Example 3). For both cholesterol and 7-dehydrocholesterol, energy was transferred between the protein tryptophanyl residues and the aromatic ring chromophores of the compounds, indicating that binding occurred in close proximity to $Trp_{19}$. A typical excitation spectrum, obtained by measuring the fluorescence of 7-dehydrocholesterol at 390 nm, is given in FIG. 6. A plot of the data that were obtained with varying cholesterol concentrations according to Equation [1] from Example 3 was similar to that for vitamin $D_3$, shown in FIG. 5. Values calculated for $K_d$ and n for cholesterol and 7-dehydrocholesterol are listed in Table 1.

EXAMPLE 6

Binding of β-Lg to Vitamin K, and Vitamin E

Studies were undertaken to evaluate whether other fat-soluble vitamins bind to β-Lg. Fluorescence emission spectra of β-Lg in the presence and absence of vitamin E, vitamin $K_1$, or vitamin $K_2$ were obtained essentially as described in Example 3.

Figure 7:
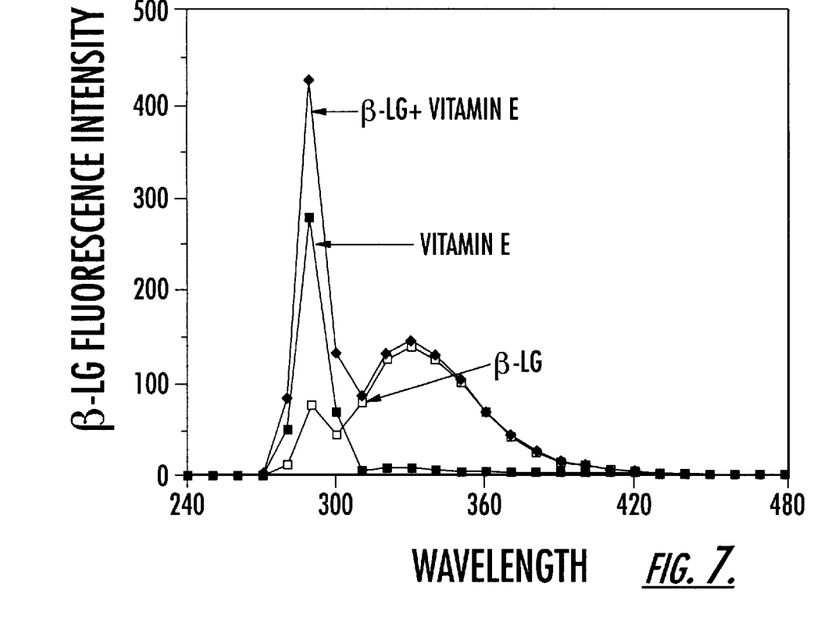
FIG. 7 is a graphical representation of the fluorescence excitation spectra of vitamin E (■) and β-Lg (□) alone or in combination (♦).

The emission spectra for β-Lg in the presence and absence of vitamin E are shown in FIG. 7. There was an increase in β-Lg fluorescence around 280 to 300 nm. The increase in fluorescence in this region of the spectrum is likely attributable to vitamin E binding to the fatty acid binding site on the surface of the β-Lg molecule. There was no change in β-Lg fluorescence in the region of 300 to 360 nm in the presence of vitamin E, because of the high background fluorescence from added vitamin.

Figure 8:
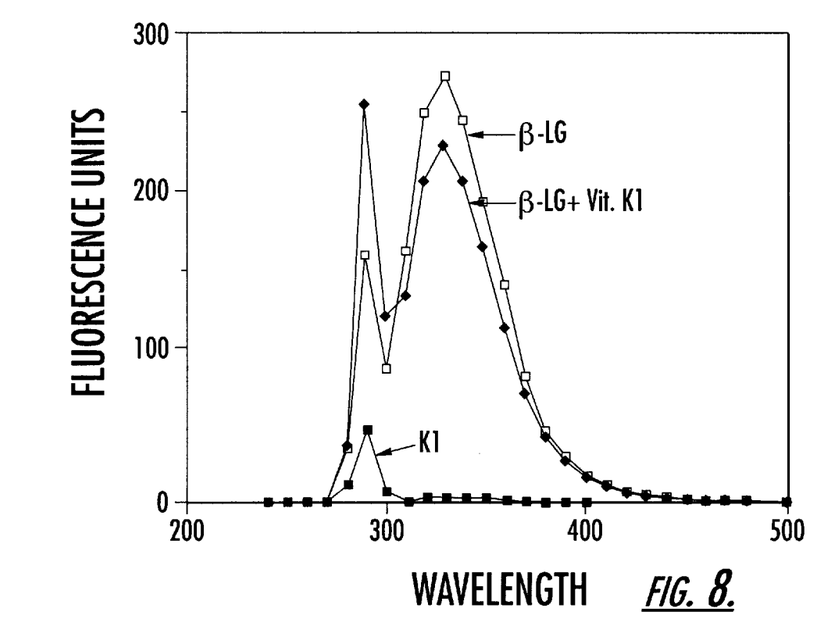
FIG. 8 is a graphical representation of the fluorescence excitation spectra of vitamin K, (■) and β-Lg (□) alone or in combination (♦).

The fluorescence emission spectra of β-Lg in the presence and absence of vitamin $K_1$ are shown in FIG. 8. The fluorescence of β-Lg was quenched between 300 and 360 nm, indicating complex formation between β-Lg and vitamin $K_1$. No quenching was seen in protein fluorescence in the presence of vitamin $K_3$ (data not shown), strongly suggesting that vitamin $K_3$ does not bind in the β-Lg calyx. In addition, there is an increase in β-Lg fluorescence in the presence of vitamin $K_1$ between 280 and 300 nm, suggesting that a second vitamin $K_1$ molecule binds to the surface fatty acid binding site. This hypothesis is supported by the stoichiometry of binding between vitamin $K_1$ and β-Lg. As discussed below, it appears that 2 molecules of vitamin $K_1$ are bound per β-Lg monomer.

The titration data were used to calculate the equilibrium dissociation constant ($K_d$) and the number of binding sites per β-Lg monomer (n), as described in Example 3. The values for $K_d$ and n are shown in Table 2 below for complexes formed between β-Lg and a variety of hydrophobic ligands, including vitamin $K_1$ and vitamin E. The $K_d$ values for vitamin $K_1$ ($K_d$=90.0) and vitamin E ($K_d$=91.0) are on the same order of magnitude ($10^{-9}$ M) as for vitamin D, vitamin A, and cholesterol. The n values indicate that only 1 molecule of vitamin E binds per β-Lg monomer (n=1), whereas 2 vitamin K, molecules bind to every β-Lg monomer (n =1.9).

TABLE 2

Binding to β-Lactoglobulin

| Ligand | $K_d$ (nM) | n (mol/mol β-LG) |
|---|---|---|
| Retinol | 35.9 | 1.0 |
| Retinoic acid | 17.0 | 0.9 |
| Palmitic acid | 490.0 | 1.2 |
| Vitamin D2 | 4.9 | 2.0 |
| Vitamin D3 | 36.0 | 2.0 |
| Cholesterol | 34.9 | 2.4 |
| Vitamin $K_1$ | 90.0 | 1.9 |
| Vitamin E | 91.0 | 1.0 |
| Retinyl palmitate (R) | 124 | 0.8 |
| Retinyl palmitate (P) | 38.7 | 1.2 |

EXAMPLE 7

Binding of β-Lg to Linoleic Acid, Conjugated Linoleic Acid, and its Methyl Ester Conjugated linoleic acid and its methyl ester are derivatives of linoleic acid, an essential fatty acid, that are produced by rumen microorganisms and are found in dairy products. Both conjugated linoleic acid and its methyl ester have been investigated for their anti-cancer effects. Further investigations were undertaken to determine whether linoleic acid, conjugated linoleic acid, and its methyl ester will bind to β-Lg.

Flourescence spectra were recorded for β-Lg in the presence and absence of linoleic acid, conjugated linoleic acid, and conjugated linoleic acid methyl ester, essentially as described in Example 3, except the temperature was held at 27° C. and 10 μM solutions of β-Lg and ligand were used. The titration data were used to calculate the equilibrium dissociation constant ($K_d$) and the number of binding sites per β-Lg monomer (n), also as described in Example 3.

Figure 9:
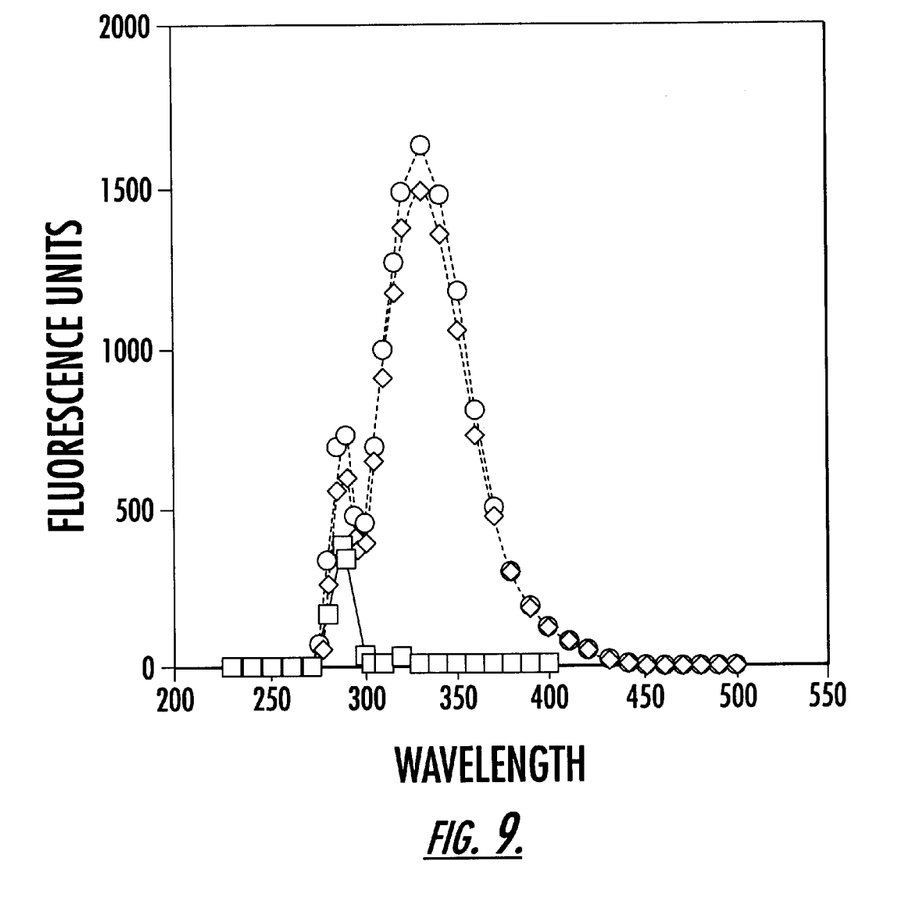
FIG. 9 is a graphical representation of the fluorescence excitation spectra of conjugated linoleic acid (□) and β-Lg (◇) alone or in combination (o). The excitation scan speed was 50 nm/mn from 200 to 500 nm. Emission was measured at 332 nm. Spectra were obtained at 27° C. with 10 μM conjugated linoleic acid in 50 mM phosphate buffer, pH 7.0, and 10 μM β-Lg.

Comparison of the emission fluorescence spectra of β-Lg and its complex with conjugated linoleic acid showed an enhancement of fluorescence intensity of $Trp_{19}$ around 332 nm. The effect of binding of conjugated linoleic acid on the fluorescence spectra of β-Lg is shown in FIG. 9. The fluorescence intensity around 332 nm is higher in the binding complex of βand conjugated linoleic acid than it is with β-Lg only. Although conjugated linoleic acid itself produced a rather strong background in the wavelength range from 260 nm to 300 nm, these emissions do not interfere with the fluorescence around 332 nm. Thus, we can be fairly certain that the enhancement in the 332 nm region is due to an interaction between conjugated linoleic acid and β-Lg. Similar results were observed with β-Lg in the presence of linoleic acid and conjugated linoleic acid methyl ester (data not shown).

The binding constants for conjugated linoleic acid or conjugated linoleic acid methyl ester and β-Lg were measured by titration as described in Example 3. Titration of β-Lg with the various ligands was quantified by following the increase in the fluorescence intensity of $Trp_{19}$ (excitation at 287 tm, emission measured at 332 nm).

The dissociation constants ($K_d$) of the binding complexes and the ratios of bound ligands to β-Lg monomers (n) were obtained for linoleic acid, conjugated linoleic acid, and its methyl ester and are shown in Table 3. The data for linoleic acid published by Frapin et al., *J. Protein Chem.* 12, 443 (1993) is also shown for comparison. The $K_d$ for linoleic acid, conjugated linoleic acid, and its methyl ester were all on the order of $10^{-7}$ M, indicating relatively strong binding between these ligands and β-Lg. The n values for all three compounds were approximately 1 molecule of ligand to one β-Lg monomer. Similar data was obtained by Scatchard analysis using a one binding site model (data not shown).

TABLE 3

Binding Parameters of Conjugated Linoleic
Acid and its Ester to β-Lactoglobulin[1]

| Ligand | n(mol/mol β-LG) | $K_d$ ($10^{-7}$ M) |
|---|---|---|
| CLA | 1.02 | 1.86 |
| CLAME | 1.03 | 1.88 |
| LA | 1.01 | 1.43 |
| LA[2] | 0.83 | 1.90 |

[1]From fluorescence enhancement of Try-19 at 332 nm of β-Lg excited at 287 nm by titration with linoleic acid (LA), conjugated linoleic acid (CLA) and its methyl ester (CLAME) at pH7.
[2]From Frapin et al., J. Protein Chem. 12,443 (1993).

EXAMPLE 8

Food Compositions Containing Complexes of D-L2 with a Lipophilic Nutrient

β-Lactoglobulin, purified by bioselective absorption as described above in Example 2, is solubilized, typically in an aqueous solution. A lipophilic nutrient is added to the β-Lg solution. The lipophilic nutrient is vitamin A (e.g., retinal, retinol, or retinoic acid), vitamin D (e.g., vitamin $D_2$ or vitamin $D_3$), vitamin E (e.g., α-tocopherol), vitamin K (e.g., vitamin $K_1$), cholesterol, linoleic acid, or linoleic acid methyl ester. The solubilized β-Lg/nutrient complex is used as a food additive for the manufacture of food compositions. The complex can also be precipitated and/or dried down to a solid form for use as a food additive. Dairy products, processed meats, breads, cakes and other bakery products, processed fruits and vegetables, etc. are manufactured containing the β-Lg/nutrient complexes. In particular, low-fat foods, and more particularly low-fat dairy foods, containing the β-Lg complexes are manufactured. Low-fat dairy foods containing the β-Lg complexes include low-fat milks (e.g., milks having 2%, 1%, 0.5% (w/w) fat or skim milk), low-fat cheeses and cheese products, low-fat yogurt, low-fat frozen desserts (e.g., ice milk, frozen yogurt), low-fat spreads, low-fat puddings and custards, and low-fat chocolates.

All patents are herein incorporated by reference in their entirety as if each individual publication or patent application was specifically and individually indicated to be incorporated by reference.

Although the foregoing invention has been described in some detail by way of illustration and example for purposes of clarity and understanding, it will be obvious that certain changes and modifications may be practiced within the scope of the appended claims.

That which is claimed is:

1. A food composition comprising a food additive comprising a preformed complex comprising β-lactoglobulin and a lipophilic nutrient selected from the group consisting of vitamin A, vitamin D, vitamin E, vitamin $K_1$, cholesterol, and conjugated linoleic acid;

wherein said β-lactoglobulin Is purified by at least 80% by bioselective absorption to an immobilized affinity ligand;

and further wherein the solubility of said lipophilic nutrient in aqueous solutions is enhanced by complex formation with said purified β-lactoglobulin.

2. A food composition according to claim 1, wherein said β-lactoglobulin is a bovine β-lactoglobulin.

3. A food composition according to claim 1, wherein said food composition is a low-fat food composition.

4. A food composition according to claim 3, wherein said low-fat food composition comprises from about 0.01 % to about 3% (w/w) fat.

5. A food composition according to claim 3, wherein said low-fat food composition is essentially a non-fat food composition.

6. A food composition according to claim 1, wherein said food composition is a dairy food composition.

7. A food composition according to claim 6, wherein said dairy food composition is a low-fat dairy food composition.

8. A food composition according to claim 7, wherein said low-fat dairy food composition is contained in a package, the interior surface of said package selected from the group consisting of polymeric surfaces and lipophilic surfaces.

9. A food composition according to claim 7, wherein said low-fat dairy food composition comprises from about 0.01% to about 3 % fat (w/w).

10. A food composition according to claim 7, wherein said low-fat dairy food composition is essentially a non-fat food composition.

11. A food composition according to claim 7, wherein said low-fat dairy food composition is a low-fat milk.

12. A food composition according to claim 11, wherein said low-fat milk is selected from the group consisting of milks having 0.5%, 1% and 2% (w/w) fat.

13. A food composition according to claim 11, wherein said low-fat food composition is skim milk.

14. A food composition according to claim 11, wherein said low-fat milk is contained in a package, the interior surface of said package selected from the group consisting of polymeric surfaces and lipophilic surfaces.

15. A food composition according to claim 11, wherein said low-fat milk is contained within a package, the interior surface of said package selected from the group consisting of polyethylene, high-density polyethylene, and wax coatings.

16. A food composition according to claim 7, wherein said low-fat dairy food composition is selected from the group consisting of low-fat milks, low-fat cheeses and cheese products, low-fat yogurts, low-fat frozen desserts, low-fat spreads, low-fat puddings, low-fat custards, and low-fat chocolates.

17. A food composition according to claim 1, wherein said food composition is an infant formula.

18. A dietary supplement comprising a preformed complex comprising β-lactoglobulin and a lipophilic nutrient selected from the group consisting of vitamin A, vitamin D, vitamin E, vitamin $K_1$, cholesterol, and conjugated linoleic acid;
   wherein said β-lactoglobulin is purified by at least 80% by bioselective absorption to an immobilized affinity ligand;
   and further wherein the solubility of said lipophilic nutrient in aqueous solutions is enhanced by complex formation with said purified P-lactoglobulin.

19. A method of manufacturing a food composition comprising β-lactoglobulin and a lipophilic nutrient, comprising the steps of:
   (a) purifying β-lactoglobulin by at least about 80% by bioselective absorption to an immobilized affinity ligand;
   (b) forming a preformed complex between the purified β-lactoglobulin of step a and a lipophilic nutrient selected from the group consisting of vitamin A, vitamin D, vitamin E, vitamin $K_1$, cholesterol, and conjugated linoleic acid, wherein the solubility of said lipophilic nutrient in aqueous solutions is enhanced by complex formation with said purified β-lactoglobulin; and
   (c) manufacturing a food composition comprising the preformed complex formed between the isolated β-lactoglobulin and the lipophilic nutrient of step b.

20. A method according to claim 19, wherein said purifying step is carried out by bioselective absorption to an immobilized retinoid.

21. A method according to claim 19, wherein said food composition is a low-fat food composition.

22. A method according to claim 19, wherein said food composition is a dairy food composition.

23. A method according to claim 22, wherein said dairy food composition is a low-fat dairy food composition.

24. A food composition produced by the method of claim 19.

25. A food composition comprising a food additive comprising a preformed complex comprising β-lactoglobulin and a lipophilic nutrient selected from the group consisting of cholesterol, vitamin $K_1$, vitamin $D_2$, and vitamin $D_3$;
   wherein said β-lactoglobulin is purified by at least 80% by bioselective absorption to an immobilized affinity ligand:
   and further wherein the solubility of said lipophilic nutrient in aqueous solutions is enhanced by complex formation with said purified β-lactoglobulin.

26. A method of manufacturing a food composition comprising β-lactoglobulin and a lipophilic nutrient, comprising the steps of:
   (a) purifying β-lactoglobulin by at least 80% by bioselective absorption to an immobilized affinity ligand;
   (b) forming a preformed complex between the purified β-lactoglobulin of step a and a lipophilic nutrient selected from the group consisting of cholesterol, vitamin $K_1$, $D_2$, and $D_3$; and
   (c) manufacturing a food composition comprising the preformed complex formed between the isolated β-lactoglobulin and the lipophilic nutrient of step b.

27. A food composition produced by the method of claim 26.

28. The food composition of claim 1, wherein said β-lactoglobulin is purified by bioselective absorption to an immobilized retinoid.

29. The dietary supplement of claim 18, wherein said β-lactoglobulin is purified by bioselective absorption to an immobilized retinoid.

30. A topical composition comprising a preformed complex comprising β-lactoglobulin and a lipophilic nutrient selected from the group consisting of vitamin A, vitamin D, vitamin E, vitamin $K_1$, cholesterol, and conjugated linoleic acid in a topical carrier;
   wherein said β-lactoglobulin is purified by at least 80% by bioselective absorption to an immobilized affinity ligand;
   and further wherein the solubility of said lipophilic nutrient in aqueous solutions is enhanced by complex formation with said purified β-lactoglobulin.

* * * * *